United States Patent [19]

Zahler

[11] Patent Number: 4,559,335

[45] Date of Patent: Dec. 17, 1985

[54] 3-ACYLAMINO-1-CARBOXYMETHYLOXY (OR THIO) CARBONYL-2-AZETIDINONES

[75] Inventor: Robert Zahler, Princeton, N.J.

[73] Assignee: E. R. Squibb & Sons, Inc., Princeton, N.J.

[21] Appl. No.: 538,720

[22] Filed: Oct. 3, 1983

[51] Int. Cl.[4] .................. C07D 205/08; C07D 403/12; C07D 401/12; A61K 31/395

[52] U.S. Cl. ............................. 514/210; 260/239 A; 260/239.3 R; 260/245.4; 260/330.3; 260/330.9; 544/182; 544/215; 544/279; 544/335; 544/336; 544/359; 544/327; 546/187; 546/208; 546/256; 546/275

[58] Field of Search ......... 260/245.4, 239 A, 239.3 R, 260/330.3, 330.9; 424/244, 270; 514/210; 544/182, 215, 279, 327, 335, 336, 359; 546/187, 208, 256, 275

[56] References Cited

FOREIGN PATENT DOCUMENTS 2141428 12/1984 United Kingdom .

Primary Examiner—Mark L. Berch
Attorney, Agent, or Firm—Lawrence S. Levinson; Donald J. Barrack

[57] ABSTRACT

Antibacterial activity is exhibited by 2-azetidinones having a 3-acylamino substituent and a 1-substituent of the formula

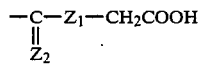

(or a salt or ester thereof), wherein $Z_1$ and $Z_2$ are each independently oxygen or sulfur.

15 Claims, No Drawings

3-ACYLAMINO-1-CARBOXYMETHYLOXY (OR THIO) CARBONYL-2-AZETIDINONES

U.S. patent application Ser. No. 515,727, filed July 27, 1983, discloses β-lactam antibiotics and intermediates comprising a 2-azetidinone having in the 1-position a group of the formula

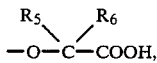

and salts and esters thereof, wherein $R_5$ and $R_6$ are as defined hereinafter.

U.S. patent application Ser. No. 252,672, filed Apr. 1, 1982, discloses β-lactam antibiotics and intermediates comprising a 2-azetidinone having in the 1-position a group of the formula

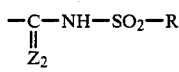

wherein $Z_2$ is as defined hereinafter and R is one of the organic substituents recited therein.

BRIEF DESCRIPTION OF THE INVENTION

Compounds having the formula

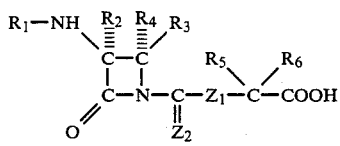

and esters and salts thereof, have antibacterial activity. In formula I, and throughout the specification, the symbols are as defined below.

$Z_1$ and $Z_2$ are each independently oxygen or sulfur;

$R_1$ is acyl;

$R_2$ is hydrogen or methoxy;

$R_3$ and $R_4$ are the same or different and each is hydrogen, alkyl, alkenyl, alkynyl, cycloalkyl, phenyl, substituted phenyl or a 4, 5, 6 or 7-membered heterocycle (referred to hereinafter as $R_x$) or one of $R_3$ and $R_4$ is hydrogen and the other is azido, halomethyl, dihalomethyl, trihalomethyl, alkoxycarbonyl, 2-phenylethenyl, 2-phenylethynyl, carboxyl, —CH$_2$X$_1$ [wherein $X_1$ is azido, amino (—NH$_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

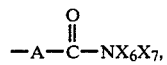

—S—X$_2$, or —O—X$_2$ (wherein A, X$_2$, X$_6$ and X$_7$ are as hereinafter defined)], —S—X$_2$ or —O—X$_2$ [wherein X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

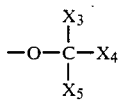

or

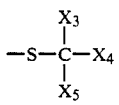

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

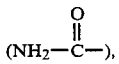

(substituted amino)carbonyl, or cyano (—C≡N)], or

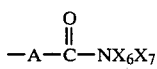

(wherein A is —CH=CH—, —(CH$_2$)$_n$—, —CH$_2$—O—, —CH$_2$—NH—, or —CH$_2$—S—CH$_2$—, n is 0, 1 or 2, and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ and $X_7$ when taken together with the nitrogen atom to which they are attached form a 4, 5, 6 or 7-membered heterocycle); and $R_5$ and $R_6$ are the same or different and each is hydrogen, alkyl, alkenyl, alkynyl, phenyl, substituted phenyl, cycloalkyl or $R_x$, or $R_5$ and $R_6$ together with the carbon atom to which they are attached are cycloalkyl or $R_x$, or =CX$_8$X$_9$ wherein $X_8$ and $X_9$ are the same or different and each is hydrogen, alkyl, phenyl or substituted phenyl, or one of $R_5$ and $R_6$ is hydrogen and the other is halomethyl, dihalomethyl, trihalomethyl, alkoxycarbonyl, alkenyl, alkynyl, 2-phenylethenyl, 2-phenylethynyl, carboxyl, —CH$_2$—X$_1$, —S—X$_2$, —O—X$_2$, or

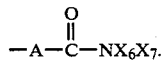

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one, or more, azido, amino (—NH$_2$), halogen, hydroxy, carboxy, cyano, alkoxycarbonyl, aminocarbonyl, alkanoyloxy, alkoxy, phenyloxy, (substituted phenyl)oxy, R$_x$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "protected carboxyl" refers to a carboxyl group which has been esterified with a conventional acid protecting group. These groups are well known in the art; see, for example U.S. Pat. No. 4,144,333, issued Mar. 13, 1979. The preferred protected carboxyl groups are benzyl, benzhydryl, t-butyl, and p-nitrobenzyl esters.

The term "substituted phenyl" refers to a phenyl group substituted with 1, 2, or 3 amino (—NH$_2$), halogen, hydroxyl, trifluoromethyl, alkyl (of 1 to 4 carbon atoms), alkoxy (of 1 to 4 carbon atoms), aminocarbonyl, or carboxyl groups.

The expression "a 4,5,6 or 7-membered heterocycle" (referred to as "R$_x$") refers to substituted and unsubstituted, aromatic and non-aromatic groups containing one or more nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

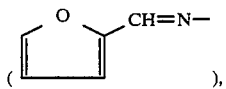

and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetinyl, oxetanyl, thietanyl, piperidinyl, piperazinyl, imidazolidinyl, oxazolidinyl, pyrrolidinyl, tetrahydropyrimidinyl, dihyrothiazolyl and hexahydroazepinyl. Exemplary of the substituted 4,5,6 or 7-membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NY$_1$Y$_2$ wherein Y$_1$ is hydrogen, alkyl, phenyl, substituted phenyl, phenylalkyl or (substituted phenyl)alkyl, and Y$_2$ is alkyl, phenyl, substituted phenyl, phenylalkyl, (substituted phenyl)alkyl, hydroxy, cyano, alkoxy, phenylalkoxy, or amino (—NH$_2$).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein R$_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

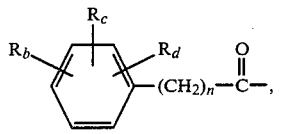

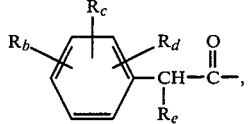

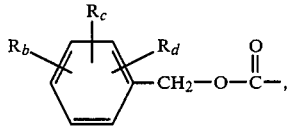

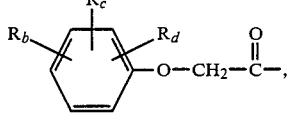

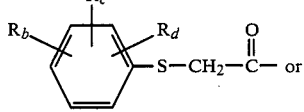

or

-continued

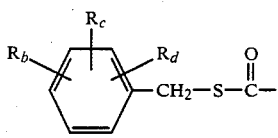

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

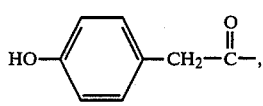

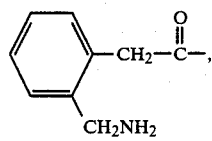

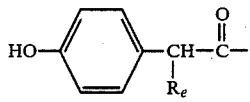

a carboxyl salt or sulfo salt) and

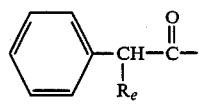

($R_e$ is preferably a carboxyl salt or sulfo salt).
(c) Heteroaromatic groups having the formula

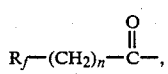

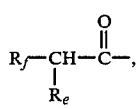

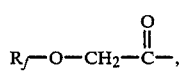

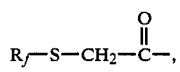

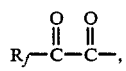

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

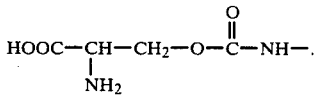

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

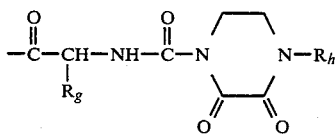

wherein $R_g$ is an aromatic group (including carbocyclic aromatics such as those of the formula

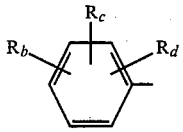

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

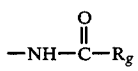

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula

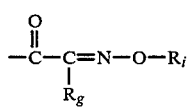

wherein $R_g$ is as defined above and $R_i$ is hydrogen, alkyl, cycloalkyl, alkylaminocarbonyl, arylaminocarbonyl (i.e.,

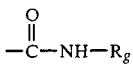

wherein R_g is as defined above) or substituted alkyl (wherein the alkyl group is substituted with one or more halogen, cyano, nitro, amino, mercapto, alkylthio, aromatic group (as defined by R_g), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

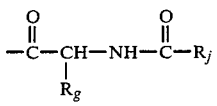

wherein $R_g$ is as defined above and $R_j$ is

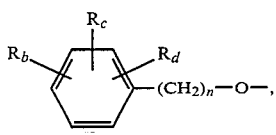

amino, alkylamino, (cyanoalkyl)amino, amido, alkylamido, (cyanoalkyl)amido,

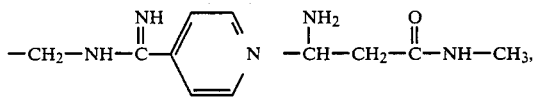

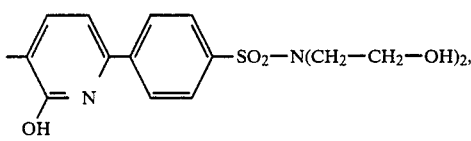

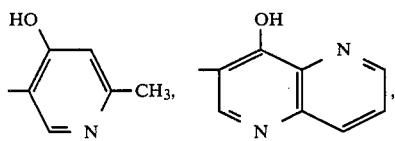

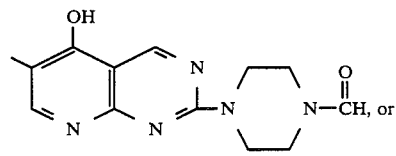

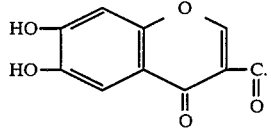

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

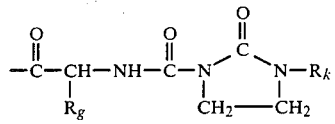

wherein $R_g$ is as defined above and $R_k$ is hydrogen, alkylsulfonyl, arylmethyleneamino (i.e., —N=CH—$R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The terms "salt" and "salts" refer to basic salts formed with inorganic and organic bases. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

As set forth throughout the specification, β-lactams having in the 1-position an ester of the group

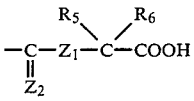

are contemplated as an integral part of this invention. Exemplary esters include alkyl, alkenyl, alkynyl, cycloalkyl, (cycloalkyl)alkyl, $R_x$-alkyl, trialkylsilylalkyl, mono-, di- or trihaloalkyl, hydroxyalkyl, alkoxyalkyl, carboxyalkyl, alkoxycarbonylalkyl, diphenylmethoxycarbonylalkyl, carbamoylalkyl, alkylcarbamoylalkyl, dialkylcarbamoylalkyl, indanyl, phenyl, substituted phenyl, phenylalkyl, (substituted phenyl)alkyl. $R_x$-carbonylalkyl, $$-\underset{\underset{Y_3}{|}}{CH}-O-\underset{\underset{}{\overset{\overset{O}{\|}}{C}}}-Y_4$$

[wherein $Y_3$ is hydrogen, alkyl or phenyl and $Y_4$ is hydrogen, alkyl, cycloalkyl, (cycloalkyl)oxy, phenyl, or alkoxy, or together $Y_3$ and $Y_4$ are $-(CH_2)_2-$, $-(CH_2)_3-$, $-CH=CH-$, or (ortho-xylylene ring structure)

], and $$-\underset{\underset{Y_3}{|}}{CH}\underset{O\overset{\overset{O}{\|}}{\diagup}\diagdown O}{\phantom{XXXX}}Y_3$$

esters.

Hydrolyzable esters are those esters that can be hydrolyzed in vivo to give the parent carboxylic acid product; they exhibit the antibiotic activity of the parent carboxylic acid. Non-hydrolyzable esters (esters that do not hydrolze in vivo to the parent carboxylic acid) are contemplated for use in this invention as intermediates; some of them are also active as antibiotics.

β-Lactams having a $$-\underset{\underset{Z_2}{\|}}{C}-Z_1-\underset{}{\overset{R_5}{\diagdown}}\underset{}{\overset{R_6}{\diagup}}\underset{}{C}-COOH$$

substituent (or an ester or salt thereof) in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

With respect to the preferred β-lactams of formula I, the structural formulas have been drawn to show the stereochemistry at the chiral center in the 3-position.

Also included within the scope of this invention are racemic mixtures which contain the above-described β-lactams.

DETAILED DESCRIPTION OF THE INVENTION

The β-lactams of formula I, and esters and salts thereof, have activity against a range of gram-negative and gram-positive organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

The products of formula I can be prepared from a 3-protected amino-2-azetidinone having the formula $$A_1-NH\underset{}{\overset{R_2}{\equiv}}\underset{}{\overset{R_4}{\equiv}}\phantom{X}II$$
$$\phantom{A_1-NH}\underset{}{\overset{\diagdown}{C}}-\underset{}{\overset{\diagup}{C}}-R_3$$
$$\phantom{A_1-NHXX}|\phantom{XX}|$$
$$\phantom{A_1-NHX}\underset{}{\overset{\diagup}{C}}-NH$$
$$\phantom{A_1-NHXX}\underset{O}{\overset{\|}{\phantom{X}}}$$

wherein the symbol "$A_1$" represents an amino protecting group (e.g., t-butoxycarbonyl, benzyloxycarbonyl, o-nitrophenylsulfenyl, etc.).

The products of formula I can be prepared by reacting a compound of formula II with a compound having the formula $$L-\underset{\underset{Z_2}{\|}}{C}-Z_1-\underset{}{\overset{R_5}{\diagdown}}\underset{}{\overset{R_6}{\diagup}}\underset{}{C}-COOA_2,\phantom{X}III$$

wherein L is a leaving group such as a halogen or imidazole and $A_2$ is a carboxyl protecting group. The reaction proceeds in the presence of a base (such as triethylamine), and yields a compound having the formula $$A_1-NH\underset{}{\overset{R_2}{\equiv}}\underset{}{\overset{R_4}{\equiv}}\phantom{XXXXXXX}IV$$
$$\phantom{A_1-NH}C-C-R_3\phantom{X}R_5\diagdown\phantom{X}R_6$$
$$\phantom{A_1-NHXX}|\phantom{XX}|\phantom{XXXXX}\diagup$$
$$\phantom{A_1-NHX}C-N-C-Z_1-C-COOA_2.$$
$$\phantom{A_1-NHX}\underset{O}{\overset{\|}{\phantom{X}}}\phantom{XXX}\underset{Z_2}{\overset{\|}{\phantom{X}}}$$

Compounds of formula III can be prepared by reacting a compound having the formula $$H-Z_1-\underset{}{\overset{R_5}{\diagdown}}\underset{}{\overset{R_6}{\diagup}}\underset{}{C}-COOA_2\phantom{X}V$$

with phosgene or thiophosgene in the presence of base (such as triethylamine or pyridine).

Alternatively, an intermediate of formula V can be prepared by reacting a compound of formula II with phosgene or thiophosgene in the presence of a base (such as triethylamine) followed by the addition of a compound of formula V in the presence of a base (such as triethylamine).

A compound of formula I can be prepared from a corresponding compound of formula IV by (i) Removing the $A_1$ and $A_2$ protecting groups simultaneously to obtain a compound having the formula

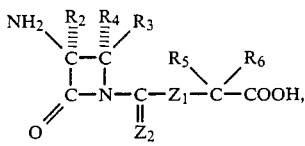

or a salt thereof, and then acylating the compound of formula VI.

(ii) Removing the $A_2$ protecting, then removing the $A_1$ protecting group, to obtain a compound of formula VI, or a salt thereof, and then acylating the compound of formula VI.

(iii) Removing the $A_1$ protecting group to obtain a compound having the formula

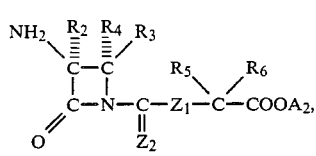

acylating the intermediate of formula VII, and then removing the $A_2$ protecting group.

The deprotection reactions can be run using art-recognized techniques. If, for example, the protecting group is t-butoxycarbonyl, trifluoroacetic acid can be used to deprotect the amino group. If the protecting group is benzyloxycarbonyl, catalytic (e.g., palladium on charcoal) hydrogenation can be used. If the protecting group is o-nitrophenylsulfenyl, p-toluenesulfonic acid can be used in combination with p-thiocresol.

The acylation reactions can also be run using art-recognized techniques. Exemplary techniques include reaction with a carboxylic acid ($R_1$—OH) or corresponding carboxylic acid halide or carboxylic acid anhydride. The reactions with a carboxylic acid proceed most readily in the presence of a carbodiimide such as dicyclohexylcarbodiimide and a substance capable of forming a reaction intermediate in situ such as N-hydroxybenzotriazole or N-hydroxysuccinimide. In those instances wherein the acyl group ($R_1$) contains reactive functionality (such as amino or carboxyl groups) it may be necessary to first protect these functional groups, then carry out the acylation reaction, and finally deprotect the resulting product.

When preparing an ester of a compound of formula I, it is also possible to choose the "$A_2$" group to correspond to the desired ester group. This avoids the need for deprotecting and then re-esterifying the carboxyl group.

Methodology for the preparation of the starting 2-azetidinones of formula II is described in United Kingdom patent application No. 2,071,650, published Sept. 23, 1981. These azetidinones are obtainable using any one of numerous procedures.

Reacting an olefin having the formula

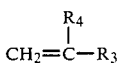

with a halosulfonylisocyanate (preferably chlorosulfonylisocyanate) having the formula

IX $O=C=N-SO_2$-halogen, yields an azetidinone having the formula

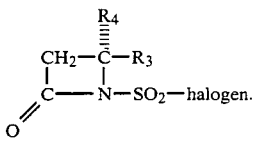

Reductive hydrolysis of an azetidinone of formula X yields an N-unsubstituted $\beta$-lactam having the formula

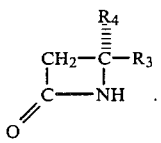

For a more detailed description of the above-described reaction sequence, reference can be made to the literature; see, for example, *Chem. Soc. Rev.*, 5, 181 (1976) and *J. Org. Chem.*, 35, 2043 (1970).

An azido group can be introduced in the 3-position of an azetidinone of formula XI by reaction of the compound with an arylsulfonyl azide (such as toluenesulfonyl azide) to obtain an azetidinone having the formula

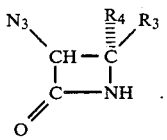

The reaction proceeds best by first protecting the azetidinone nitrogen with a silyl residue (e.g., t-butyldimethylsilyl, or t-butyldiphenylsilyl), then generating the anion at the 3-position of the nucleus with a strong organic base (e.g., lithium diisopropylamine) at a low temperature, and then treating the anion with toluenesulfonyl azide. The resulting intermediate is quenched with trimethylsilyl chloride, and subsequent acid hydrolysis or fluoride solvolysis of the N-protecting group yields the compound of formula XII.

A 3-azido-2-azetidinone of formula XII wherein $R_4$ is hydrogen can also be prepared by first reacting a primary amine having the formula

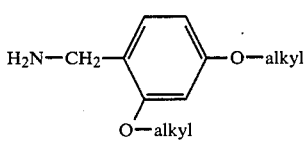

or

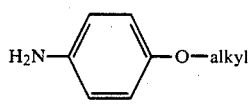

with an aldehyde having the formula

 XV (or a hemiacetal) to yield the corresponding Schiff base. A [2+2] cycloaddition reaction of the Schiff base with an activated form of α-azidoacetic acid yields a 3-azido-2-azetidinone having the formula

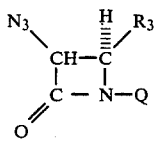 XVI wherein Q is

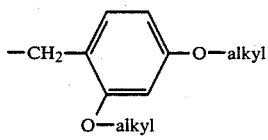

or

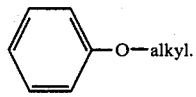

Oxidative removal of the 1-substituent yields the corresponding compound having the formula

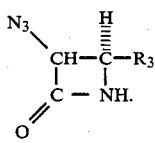 XVII

A 3-azido-2-azetidinone of formula XII or XVII can be reduced to the corresponding 3-amino-2-azetidinone having the formula

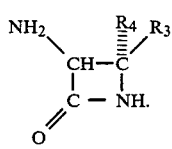 XVIII

The reduction can be accomplished by catalytic (e.g., palladium on charcoal, or platinum oxide) hydrogenation or with reducing agents such as zinc or triphenylphosphine. A 3-amino-2-azetidinone can be converted to a corresponding 3-protected amino-2-azetidinone of formula II using art-recognized techniques.

A compound of formula II wherein $R_3$ is hydrogen can also be obtained using a procedure analogous to that described above for the preparation of a 3-azido-2-azetidinone wherein $R_3$ is hydrogen. In place of an activated form of α-azidoacetic acid, an activated form of α-phthalimidoacetic acid is used, yielding a compound having the formula

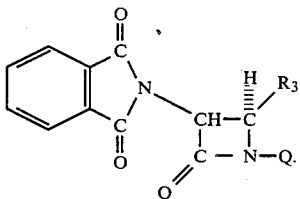 XIX

Treatment of a compound of formula XIX with base yields the corresponding 4α compound having the formula

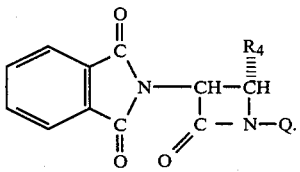 XX

Reaction of a compound of formula XIX or XX with a reagent such as methyl hydrazine (to cleave the phthaloyl group), followed by the introduction of a protecting group on the 3-nitrogen substituent, and oxidative removal of the 1-protecting group will yield a compound of formula II wherein $R_2$ and $R_4$ are hydrogen.

The starting 2-azetidinones of formula II wherein $R_2$ is methoxy can be prepared by methoxylating the corresponding non-methoxylated compound of formula II. Chlorination of a non-methoxylated compound of formula II yields a compound having the formula

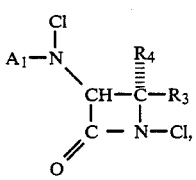 XXI and can be accomplished by reaction of a compound of formula II with a reagent such as t-butyl hypochlorite, sodium hypochlorite, chlorine or other reagent useful for N-chlorinating amides. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of a compound of formula XXI with a methoxylating agent, e.g., an alkali metal methoxide, and subsequently adding a reducing agent such as trimethylphosphite, yields a compound having the formula

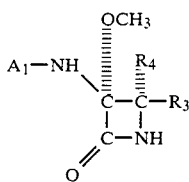

in combination with its enantiomers.

Additional methodology for the preparation of the starting 2-azetidinones of formula II is described in United Kingdom patent application No. 2,071,650, published Sept. 23, 1981. The cyclization of amino acids to yield 2-azetidinones is described as is the degradation of 6-amino-penicillanic acids and 7-aminopenicillanic acids to yield 2-azetidinones.

The following examples are specific embodiments of this invention.

EXAMPLE 1

[3S(Z)]-3-[[(2-Amino-4-thiazolyl)(methoxyimino)-acetyl]amino]-2-oxo-1-azetidinecarboxylic acid, carboxymethyl ester (A) (S)-3-[[(Phenylmethoxy)carbonyl]amino]-2-oxo-1-azetidinecarboxylic acid, [(phenylmethoxy)-carbonyl]methyl ester To 332 mg (2.0 mmol) of benzyl glycolate was added 2.9 ml of 12.5% phosgene (in toluene) at 0° C. To this solution at 0° C. was added pyridine (0.186 ml, 2.3 mmol) dropwise. The reaction was allowed to stir at room temperature for 1 hour and was then filtered under argon. The filtrate was evaporated, and the residue was dissolved in methylene chloride (4 ml). To this solution was added (S)-3-[[(t-butyloxy)carbonyl]amino]-2-azetidinone, and the resulting suspension was cooled to −30° C. Triethylamine (0.293 ml, 2.1 mmol) was then added dropwise, and after 2 hours the product was extracted from 0.5M $KH_2PO_4$ with three portions of ethyl acetate. The combined organic layers were dried over sodium sulfate, and the volatiles were removed. The residue was subjected to column chromatography on silica gel (eluting with 40% ethyl acetate-hexane) to yield 148 mg of the title compound.

(B) [3S(Z)-3-[[(2-Amino-4-thiazolyl)-(methoxyimino)acetyl]amino]-2-oxo-1-azetidinecarboxylic acid, carboxymethyl ester Diisopropylethylamine (0.184 ml, 1.06 mmol) was added to 193 mg (0.96 mmol) of (Z)-2-amino-α-(methoxyimino)-4-thiazoleacetic acid in 3 ml of dimethylformamide at 23° C. The mixture was cooled to −20° C., and diphenyl chlorophosphate (0.199 ml, 0.96 mmol) was added. The resulting mixture was stirred for 30 minutes to yield a mixed anhydride.

(S)-3-[[(Phenylmethoxy)carbonyl]amino]-2-oxo-1-azetidinecarboxylic acid, [(phenylmethoxy)-carbonyl]-methyl ester (329 mg, 0.80 mmol) was dissolved in 3 ml of dimethylformamide followed by the sequential addition of 10% palladium on charcoal (165 mg) and p-toluenesulfonic acid, monohydrate (152 mg, 0.80 mmol). This mixture was subjected to hydrogenolysis (23° C., 1 atm) for 2 hours. Upon cooling to 0° C., diisopropylethylamine (0.460 ml, 2.64 mmol) was added, immediately followed by the above mixed anhydride. The reaction was stirred at 5° C. overnight.

The volatiles were removed under vacuum. The residue was subjected to column chromatography with water on Dowex 50X2*-400 resin (K+ form), followed by chromatography on HP-20** (eluting with water) to give the title compound contaminated with potassium p-toluenesulfonate. This material was dissolved in water, and the pH was adjusted to 2.5. Chromatography on HP-20 (eluting with water, 5% acetone-water, and 10% acetone-water) yielded 47 mg of the title compound, melting point 215° C., dec.

*Dowex 50X2 is a strongly acidic cation exchange resin made by the nuclear sulfonation of styrene-divinylbenzene beads containing 2% divinylbenzene and 98% styrene and other monovinyl monomers.
**HP-20 is a macroporous styrene-divinylbenzene copolymer manufactured by Mitsubishi Chemical Industries.

EXAMPLE 2

[3S-[3α(Z),4β]]-3-[[(2-Amino-4-thiazolyl)-(methoxyimino)acetyl]amino]-4-methyl-2-oxo-1-azetidinecarboxylic acid, carboxymethyl ester, potassium salt (A) (3S-trans)-3-[[(t-Butyloxy)carbonyl]amino]-4-methyl-2-oxo-1-azetidinecarboxylic acid, [(phenylmethoxy)carbonyl]methyl ester To 664 mg (4.0 mmol) of benzyl glycolate was added 5.8 ml of 12.5% phosgene (in toluene) at 0° C. To this solution at 0° C. was added pyridine (0.372 ml, 4.6 mmol) dropwise. The reaction was allowed to stir at room temperature for 2 hours and was then filtered under argon. Most of the volatiles were removed under vacuum without external heating, and the residual chloroformate was dissolved in methylene chloride (8 ml). Approximately half of this solution was added to (3S-trans)-3-[[(t-butyloxy)carbonyl]amino]-4-methyl-2-azetidinone (440 mg, 2.0 mmol), and the resulting solution was cooled to −20° C. Triethylamine (0.293 ml, 2.1 mmol) was then added dropwise. After 2 hours at −20° C., the remaining chloroformate was added to the azetidinone reaction mixture followed by 0.293 ml of triethylamine. After 3 hours at −20° C., the product was extracted from aqueous $KH_2PO_4$ with three portions of ethyl acetate. The combined organic layers were dried over sodium sulfate, and the volatiles were removed. The residue was subjected to column chromatography on silica gel (eluting with 35% ethyl acetate-hexane) to yield 488 mg of the title compound.

(B) [3S-[3α(Z),4β]]-3-[[(2-Amino-4-thiazolyl)-(methoxyimino)acetyl]amino]-4-methyl-2-oxo-1-azetidinecarboxylic acid, carboxymethyl ester, potassium salt Diisopropylethylamine (0.345 ml, 1.98 mmol) was added to 363 mg (1.80 mmol) of (Z)-2-amino-α-(methoxyimino)-4-thiazoleacetic acid in 6 ml of dimethylformamide at 23° C. The mixture was cooled to −20° C. and diphenyl chlorophosphate (0.373 ml, 1.80 mmol) was added. The resulting mixture was stirred for 30 minutes to yield a mixed anhydride.

(3S-trans)-3-[[(t-Butyloxy)carbonyl]amino]-4-methyl-2-oxo-1-azetidinecarboxylic acid, [(phenylmethoxy)carbonyl]methyl ester (584 mg, 1.49 mmol) was dissolved in 5 ml of acetonitrile. Hydrogenolysis for 1.5 hours (23° C., 1 atm) in the presence of 10% palladium on charcoal (292 mg) removed the benzyl protecting group. The reaction mixture was filtered and the volatiles were removed. The residue was dissolved in 7.7 ml of 10% anisole-trifluoroacetic acid at 0° C. After 40 minutes, the trifluoroacetic acid was evaporated, and the residue was triturated with hexane and ether. The remaining material was dissolved in 5 ml of dimethylformamide and cooled to 0° C. Diisopropylethylamine (1.25 ml) was then added to the azetidinone solution, immediately followed by the mixed anhydride. The reaction was stirred at 0° C. for 1.5 hours and placed at −20° C.

overnight. The volatiles were removed under vacuum. The residue was subjected to column chromatography with water on Dowex 50X2-400 resin (K+ form), followed by chromatography on HP-20 (eluting with water) to give 65 mg of the title compound, melting point 200° C., dec.

What is claimed is:

1. A compound having the formula

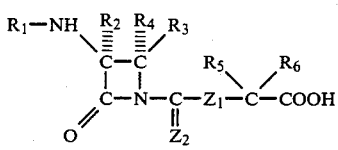

or a pharmaceutically acceptable ester or basic salt thereof, wherein $Z_1$ and $Z_2$ are each independently oxygen or sulfur;

$R_1$ is an acyl group derived from a carboxylic acid;

$R_2$ is hydrogen or methoxy;

$R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, —$CH_2X_1$, carboxyl, —S—$X_2$, —O—$X_2$,

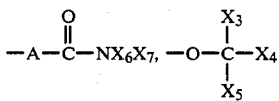

or

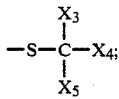

wherein $X_1$ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)-sulfonyloxy, phenyl, substituted phenyl, cyano,

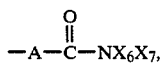

—S—$X_2$ or —O—$X_2$; $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH═CH—, —$(CH_2)_n$—, —$CH_2$—O—, —$CH_2$—NH— or —$CH_2$—S—$CH_2$—; n is 0, 1 or 2; and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ and $X_7$ when taken together with the nitrogen atom to which they are attached form a 4, 5, 6 or 7-membered heterocycle; and $R_5$ and $R_6$ are the same or different and each is hydrogen, alkyl, alkenyl, alkynyl, phenyl, substituted phenyl, cycloalkyl or a 4, 5, 6 or 7-membered heterocycle, or $R_5$ and $R_6$ together with the carbon atom to which they are attached are cycloalkyl or a 4, 5, 6 or 7-membered heterocycle, or =$CX_8X_9$ wherein $X_8$ and $X_9$ are the same or different and each is hydrogen, alkyl, phenyl or substituted phenyl, or one of $R_5$ and $R_6$ is hydrogen and the other is halomethyl, dihalomethyl, trihalomethyl, alkoxycarbonyl, alkenyl, alkynyl, 2-phenylethenyl, 2-phenylethynyl, carboxyl, —$CH_2$—$X_1$, —S—$X_2$, —O—$X_2$, or

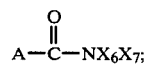

wherein the terms "alkyl" and "alkoxy" refer to groups having 1 to 10 carbon atoms;

the terms "cycloalkyl" and "cycloalkenyl" refer to groups having 3, 4, 5, 6 or 7 carbon atoms:

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups;

the terms "alkanoyl", alkenyl" and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, aminocarbonyl, or carboxyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, or tetrazolyl, or one of the above groups substituted with one or more halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino, or substituted alkyl, wherein the alkyl group has 1 to 4 carbons, groups;

the term "a 4,5,6 or 7-membered heterocycle" refers to pyridinyl, furanyl, pyrrolyl, thienyl 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or to one of the above groups substituted with one or more oxo, halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino, or substituted alkyl, wherein the alkyl group has 1 to 4 carbons, groups;

the term "substituted amino" refers to a group having the formula —$NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy, or amino.

2. A compound in accordance with claim 1 wherein $Z_2$ is oxygen.

3. A compound in accordance with claim 1 wherein $Z_2$ is sulfur.

4. A compound in accordance with claim 2 wherein $Z_1$ is oxygen.

5. A compound in accordance with claim 2 wherein $Z_1$ is sulfur.

6. A compound in accordance with claim 4 wherein $R_2$ is hydrogen.

7. A compound in accordance with claim 5 wherein $R_2$ is hydrogen.

8. A compound in accordance with claim 6 wherein $R_3$, $R_4$, $R_5$ and $R_6$ are each independently hydrogen or methyl.

9. A compound in accordance with claim 6 wherein one of $R_3$ and $R_4$ is hydrogen and the other is methyl, and $R_5$ and $R_6$ are each hydrogen.

10. A compound in accordance with claim 5 wherein $R_3$, $R_4$, $R_5$ and $R_6$ are each independently hydrogen or methyl.

11. A compound in accordance with claim 6 wherein $R_3$, $R_4$, $R_5$ and $R_6$ are each hydrogen.

12. A compound in accordance with claim 5 wherein $R_3$, $R_4$, $R_5$ and $R_6$ are each hydrogen.

13. A compound in accordance with claim 1 wherein $R_1$ is

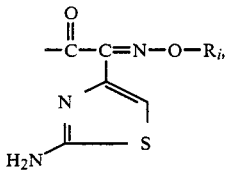

and $R_i$ is methyl, ethyl, carboxymethyl, 1-carboxy-1-methylethyl, 2,2,2-trifluoroethyl or 1-carboxycyclopropyl.

14. A compound in accordance with claim 2 wherein $R_1$ is

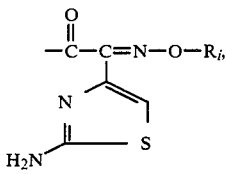

and $R_i$ is methyl, ethyl, carboxymethyl, 1-carboxy-1-methylethyl, 2,2,2-trifluoroethyl or 1-carboxycyclopropyl.

15. A compound having the formula

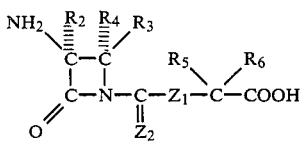

or a basic salt thereof, or a benzyl, benzhydryl, t-butyl or p-nitrobenzyl ester thereof, wherein $Z_1$ and $Z_2$ are each independently oxygen or sulfur;

$R_2$ is hydrogen or methoxy;

$R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, —CH$_2$X$_1$, carboxyl, —S—X$_2$, —O—X$_2$,

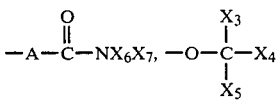

or

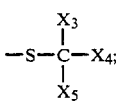

wherein $X_1$ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

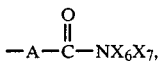

—S—X$_2$ or —O—X$_2$; $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH═CH—, —(CH$_2$)$_n$—, —CH$_2$—O—, —CH$_2$—NH— or —CH$_2$—S—CH$_2$—; n is 0, 1 or 2; and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ and $X_7$ when taken together with the nitrogen atom to which they are attached form a 4, 5, 6 or 7-membered heterocycle; and $R_5$ and $R_6$ are the same or different and each is hydrogen, alkyl, alkenyl, alkynyl, phenyl, substituted phenyl, cycloalkyl or a 4, 5, 6 or 7-membered heterocycle, or $R_5$ and $R_6$ together with the carbon atom to which they are attached are cycloalkyl or a 4, 5, 6 or 7-membered heterocycle, or ═CX$_8$X$_9$ wherein $X_8$ and $X_9$ are the same or different and each is hydrogen, alkyl, phenyl or substituted phenyl, or one of $R_5$ and $R_6$ is hydrogen and the other is halomethyl, dihalomethyl, trihalomethyl, alkoxycarbonyl, alkenyl, alkynyl, 2-phenylethenyl, 2-phenylethynyl, carboxyl, —CH$_2$—X$_1$, —S—X$_2$, —O—X$_2$, or

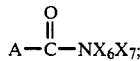

wherein the terms "alkyl" and "alkoxy" refer to groups having 1 to 10 carbon atoms;

the terms "cycloalkyl" and "cycloalkenyl" refer to groups having 3, 4, 5, 6 or 7 carbon atoms:

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups;

the terms "alkanoyl", alkenyl" and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, aminocarbonyl, or carboxyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, or tetrazolyl, or one of the above groups substituted with one or more halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino, or substituted alkyl, wherein the alkyl group has 1 to 4 carbons, groups;

the term "a 4,5,6 or 7-membered heterocycle" refers to pyridinyl, furanyl, pyrrolyl, thienyl 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or to one of the above groups substituted with one or more oxo, halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino, or substituted alkyl, wherein the alkyl group has 1 to 4 carbons, groups;

the term "substituted amino refers to a group having the formula —NY$_1$Y$_2$ wherein Y$_1$ is hydrogen, alkyl, phenl, substituted phenyl, phenylalkyl or (substituted phenyl)alkyl, and Y$_2$ is alkyl, phenyl, substituted phenyl, phenylalkyl, (substituted phenyl)alkyl, hydroxy, cyano, alkoxy, phenylalkoxy, or amino.

* * * * *

UNITED STATES PATENT AND TRADEMARK OFFICE
CERTIFICATE OF CORRECTION

PATENT NO. : 4,559,335
DATED : December 17, 1985
INVENTOR(S) : Robert Zahler

It is certified that error appears in the above-identified patent and that said Letters Patent is hereby corrected as shown below:

Column 5, lines 33 and 40, after the structural formula, add -- ($R_e$ is preferably --.

Column 22, line 25, "phenl" should read -- phenyl --.

Signed and Sealed this

Fifteenth Day of April 1986

[SEAL]

Attest:

DONALD J. QUIGG

Attesting Officer

Commissioner of Patents and Trademarks